United States Patent [19]

Li et al.

[11] Patent Number: 5,602,272
[45] Date of Patent: Feb. 11, 1997

[54] REDUCTION AND RESOLUTION METHODS FOR THE PREPARATION OF COMPOUNDS USEFUL AS INTEMEDIATES FOR PREPARING TAXANES

[75] Inventors: Wen-Sen Li, Marlboro; John K. Thottathil, Robbinsville, both of N.J.

[73] Assignee: Bristol-Myers Squibb Company, Princeton, N.J.

[21] Appl. No.: 263,869

[22] Filed: Jun. 21, 1994

[51] Int. Cl.$^6$ ................................................. C07C 229/00
[52] U.S. Cl. ................................................. 560/39; 562/444
[58] Field of Search ............................... 560/39; 562/444

[56] References Cited

U.S. PATENT DOCUMENTS

| | | |
|---|---|---|
| 4,584,270 | 4/1986 | Sih . |
| 4,800,162 | 1/1989 | Matson . |
| 4,814,470 | 3/1989 | Colin et al. . |
| 4,857,468 | 8/1989 | Kutsuki et al. . |
| 4,857,653 | 8/1989 | Colin et al. . |
| 4,876,399 | 10/1989 | Holton et al. . |
| 4,924,011 | 5/1990 | Denis et al. . |
| 4,924,012 | 5/1990 | Colin et al. . |
| 5,064,761 | 11/1991 | Schneider et al. . |

FOREIGN PATENT DOCUMENTS

| | | |
|---|---|---|
| 0414610A1 | 2/1991 | European Pat. Off. . |
| 552041 | 7/1993 | European Pat. Off. . |
| 634492 | 1/1995 | European Pat. Off. . |
| 0385172A1 | 9/1990 | France . |
| 0400971A2 | 12/1990 | France . |
| 92/12140 | 7/1992 | WIPO . |

OTHER PUBLICATIONS

Nakamura, et al., Stereoselective Preparation of (R)–4–Nitro–2–butanol and (R)–5–Nitro–2–pentanol Mediated by a Lipase; *Agric Biol. Chem.*, 54(6), pp. 1569–1570 (1990).

Kingston, The Chemistry of Taxol, *Pharm. Ther.*, vol. 52, pp. 1–34 (1991).

Sih, et al., Mikrobielle asymmetrische Katalyze–enantioselektive Reduktion von Ketonen; *Angew Chem.*, 96, pp. 556–565 (1984).

Georg, et al., Asymmetric Synthesis of β–Lactams and N–Benzoyl–3–Phenylisoserines via the Staudinger Reaction, *Tetrahedron Letters*, vol. 32, No. 27, pp. 3151–3154 (1991).

Denis, et al., An Efficient, Enantioselective Synthesis of the Taxol Side Chain, *J. Org. Chem.*, 51, pp. 46–50 (1986).

Honig, et al., Chemo–Enzymatic Synthesis of All Isomeric 3–Phenylserines and –Isoserines, *Tetrahedron*, vol. 46, No. 11, pp. 3841–3850 (1990).

Fones, The Isomers of the β–phenylserines, *J. Biol. Chem.*, 204, pp. 323–328 (1953).

Denis, et al., An Improved Synthesis of the Taxol Side Chain and of RP 56976; *J. Org. Chem.*, 55, pp.1957–1959 (1990).

Ojima, et al., Efficient and Practical Asymmetric Synthesis of the Taxol C–13 Side Chain, N–Benzoyl–(2R, 3S)–3–phenylisoserine, and Its Analogues via Chiral 3–Hydroxy–4–aryl–β–lactams through Chiral Ester Enolate–Imine Cyclo–condensation, *J. Org. Chem.*, 56, pp. 1681–1683 (1991).

Imuta, et al., Product Stereospecificity in the Microbial Reduction of α–Haloaryl Ketones, *J. Org. Chem.*, 45, pp. 3352–3355 (1980).

Ohta, et al., Microbial Reduction of 1,2–Diketones to Optically Active α–Hydroxyketones; *Agric. Biol. Chem.*, 51(9), pp. 2421–2427 (1987).

Hummel, Reduction of acetophenone to R(+)–phenylethanol by a new alcohol dehydrogenase from *Lactobacillus kefir*, *Appl. Microbial Biotechnol*, 34, pp. 15–19 (1990).

Shen, et al., A New NAD–dependent Alcohol Dehydrogenase with Opposite Facial Selectivity useful for Asymmetric Reduction and Cofactor Regeneration, *J. Chem. Soc. Chem. Commun.*, pp. 677–679 (1990).

Christen, et al., Biotransformation in Organic Synthesis: Applications of Yeast Reduction in the Synthesis of 3,5–Dihydroxy Esters of High Optical Purity, *J. Chem. Soc., Chem. Commun.*, pp. 264–266 (1988).

Fujisawa, et al., Diastereo–and Enantioselective Reduction of α, β–Diketodithiane with the Baker's Yeast, *Tetrahedron Letters*, vol. 26, No. 49, pp. 6089–6092 (1985).

Willaert, et al., Enzymatic in Vitro Reduction of Ketones; *Bioorganic Chemistry*, pp. 223–231 (1988).

Hoffmann, et al., Synthesis of 6S,7S–Anhydro–Serricornine, *Tetrahedron Letters*, vol. 23, No. 34, pp. 3479–3482 (1982).

Bernardi, et al., Production of (R)–1,(1, 3–Dithian–2–yl)propan–2–ol by Microbial Reduction; *J. Chem. Soc.*, Perkin Trans. I, pp. 1607–1608 (1987).

Chunduru, et al., Mechanism of Ketol Acid Reductoisomerase—Steady–State Analysis and Metal Ion Requirement, *Biochemistry*, vol. 28, No. 2, pp. 486–493 (1989).

Utaka, et al., Asymmetric Reduction of a Prochiral Carbonyl Group of Aliphatic γ–and δ Keto Acids by Use of Fermenting Bakers' Yeast, *J. Org. Chem.*, vol. 52, pp. 4363–4368 (1987).

Dale, et al., α–Methoxy–α–trifluoromethylphenylacetic Acid, a Versatile Reagent for the Determination of Enantiomeric Composition of Alcohols and Amines; *The J. of Org. Chem.*, vol. 34, No. 9, pp. 2543–2550 (1969).

Naoshima, et al., Biotransformation of Some Keto Esters through the Consecutive Reuse of Immobolized *Nicotiana tabacum* Cells; *J. Org. Chem.*, vol. 54, pp. 4237–4239 (1989).

(List continued on next page.)

*Primary Examiner*—Samuel Barts
*Attorney, Agent, or Firm*—Suzanne E. Babajko

[57] ABSTRACT

Reduction and resolution methods for the preparation of compounds useful as intermediates in the preparation of taxanes, and particularly for preparation of desired stereoisomers for use in the formation of the C-13 sidechain of pharmaceutically useful taxanes such as paclitaxel.

13 Claims, No Drawings

OTHER PUBLICATIONS

Bucciarelli, et al., Asymmetric Reduction of Trifluoromethyl and Methyl Ketones by Yeast; An Improved Method; *Synthesis Communications*, pp. 897–899 (1983).

Charles, et al., Bicyclic Heterocycles with Nitrogen at the Ring Junction. Part 2. Application of the Dakin–West Reaction to the Synthesis of Imidazo[5,1-f]-1,2,4-triazin-4(3H)-ones, *J.C.S. Perkin I*, pp. 1139–1145 (1980).

Denis, et al., A Highly Efficient, Practical Approach to Natural Taxol, *J. Am. Chem. Soc.*, 110, 5917–5919 (1988).

Deng et al., A Practical, Highly Enantioselective Synthesis of the Taxol Side Chain via Asymmetric Catalysis; *J. Org. Chem.*, 57, pp. 4320–4323 (1992).

Holton, et al., A Synthesis of Taxusin, *J. Am. Chem. Soc.*, 110, pp. 6558–6560 (1988).

Angelastro et al., $\alpha$–Diketone and $\alpha$–Keto Ester Derivatives of N–Protected Amino Acids and Peptides as Novel Inhibitors of Cysteine and Serine Proteases, *J. Med. Chem.*, 33(1), pp. 11–13 (1990).

Magri et al., Modified Taxols. 2. Oxidation Products of Taxol, *J. Org. Chem.*, 51(6), pp. 797–802 (1986).

5,602,272

REDUCTION AND RESOLUTION METHODS FOR THE PREPARATION OF COMPOUNDS USEFUL AS INTEMEDIATES FOR PREPARING TAXANES

FIELD OF THE INVENTION

The present invention relates to reduction and resolution methods for the preparation of compounds useful as intermediates in the preparation of taxanes, and particularly to the preparation of desired stereoisomers of such intermediate compounds for use in the formation of the C-13 sidechain of pharmaceutically useful taxanes.

BACKGROUND OF THE INVENTION

Taxanes are diterpene compounds which find utility in the pharmaceutical field. For example, paclitaxel (Taxol®), a taxane having the structure:

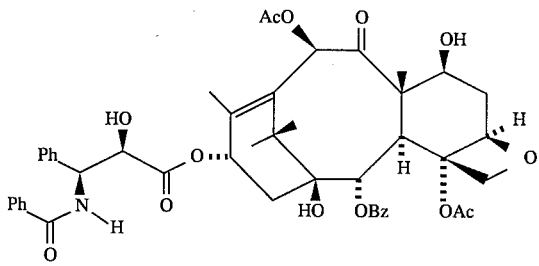

where Ph is phenyl, Ac is acetyl and Bz is benzoyl, has been found to be an effective anticancer agent. Naturally occurring taxanes such as paclitaxel may be found in plant materials, and have been isolated therefrom. Such taxanes may, however, be present in plant materials in relatively small amounts so that, in the case of paclitaxel, for example, large numbers of the slow-growing yew trees forming a source for the compound may be required.

Although certain semi-synthetic routes for the preparation of taxanes such as paclitaxel and analogs thereof have been described, more efficient methods continue to be sought in the art. In this regard, routes are sought for the preparation of intermediates useful in forming the C-13 sidechain of pharmaceutically useful taxanes, particularly such compounds having a desired stereoconfiguration.

SUMMARY OF THE INVENTION

The present invention provides methods for the chemical reduction of keto group-containing compounds to form hydroxyl group-containing compounds, and for the resolution of enantiomeric, especially racemic mixtures of the hydroxyl group-containing compounds. The methods of the present invention provide a simple and efficient route for obtaining chiral hydroxyl group-containing compounds useful as intermediates in the preparation of C-13 sidechain bearing taxanes such as paclitaxel and analogs thereof.

In particular, the present invention provides a method for the chemical reduction of a compound of the formula I:

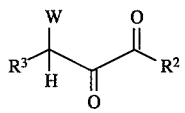 (I)

to form a compound of the formula II:

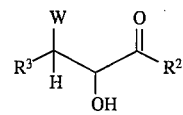 (II)

where

W is $-N_3$; $-NHR^5$; or $-NH-C(O)-R^1$;

$R^1$ is $-R^5$; $-O-R^7$; $-S-R^7$; or $-N-(R^5)(R^6)$;

$R^2$ is $-O-R^5$;

$R^3$ is $-R^5$;

$R^5$ and $R^6$ are each independently hydrogen; alkyl; alkenyl; alkynyl; cycloalkyl; cycloalkenyl; aryl; or heterocyclo; and $R^7$ is alkyl; alkenyl; alkynyl; cycloalkyl; cycloalkenyl; aryl; or heterocyclo;

comprising the steps of contacting said compound of the formula I with a reducing agent capable of reducing said compound of the formula I to form said compound of the formula II, and effecting said reduction.

In the compounds of the formula I, the groups W and $R^3$ are bonded to an asymmetric carbon atom, the stereoconfiguration of which is retained during the present reduction reaction. Thus, where the starting compound of the formula I comprises a stereoisomeric mixture, such as a racemate of R and S compounds with respect to the aforementioned asymmetric carbon, that mixture is retained in the formula II product. Further, an additional asymmetric carbon with R and S stereoisomerism is formed by the reduction of the carbonyl group of the formula I starting material to the group —CH(OH)— of the formula II product. Thus, the formula II product may be present in one or more of the following stereoisomeric forms IIa through IId:

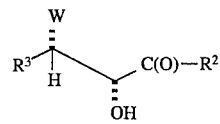 (IIa)

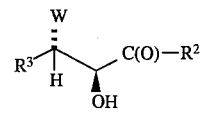 (IIb)

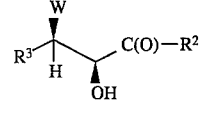 (IIc)

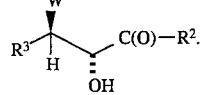 (IId)

Compounds of the formula IIa have the same absolute stereoconfiguration, at the carbon atom bearing the groups W and $R^3$, and the carbon atom bearing the hydroxyl group formed by the reduction process, as the compound (2R,3S)-(−)-N-benzoyl-3-phenylisoserine ethyl ester; compounds of the formula IIb have the same absolute stereoconfiguration at the corresponding carbon atoms as the compound (2S,3S)-(−)-N-benzoyl-3-phenylisoserine ethyl ester; compounds of the formula IIc have the same absolute stereoconfiguration at the corresponding carbon atoms as the compound (2S,3R)-(−)-N-benzoyl-3-phenylisoserine ethyl ester; and compounds of the formula IId have the same absolute stereoconfiguration at the corresponding carbon atoms as the compound (2R,3R)-(−)-N-benzoyl-3-phenylisoserine ethyl ester. Compounds of the formulae IIa and IIc are referred to herein as "syn" enantiomers; compounds of the formulae IIb and IId are referred to herein as "anti" enantiomers.

As chiral compounds of the formula II are preferred as intermediates in the preparation of pharmaceutically useful taxanes, it may be desirable to separate the mixture of formula II stereoisomers, most preferably into a form where the formula II stereoisomer sought is substantially free of other stereoisomers of the formula II.

The present invention also provides a resolution method for the separation of an enantiomeric mixture of stereoisomers of the formula II, comprising the step of contacting said enantiomeric mixture with an optically active agent to form a mixture of diastereomeric salts. It is preferred, upon formation of the mixture of diastereomeric salts, to separate the salts, and further, to regenerate the starting compound II from at least one of the separated salts.

DETAILED DESCRIPTION OF THE INVENTION

The methods of the present invention are described further as follows. Unless otherwise indicated, salts or solvates, such as hydrates, of reactants or products may be employed or prepared as appropriate in any of the methods of the present invention.

The terms "alkyl" or "alk", as used herein alone or as part of another group, denote optionally substituted, straight and branched chain saturated hydrocarbon groups, preferably having 1 to 12 carbons in the normal chain. Exemplary unsubstituted such groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl and the like. Exemplary substituents may include one or more of the following groups: halo, alkoxy, alkylthio, alkenyl, alkynyl, aryl, cycloalkyl, cycloalkenyl, hydroxy or protected hydroxy, carboxyl (—COOH), alkyloxycarbonyl, alkylcarbonyloxy, carbamoyl ($NH_2$—CO—), amino (—$NH_2$), mono- or dialkylamino, or thiol (—SH).

The terms "lower alk" or "lower alkyl" as used herein, denote such optionally substituted groups as described above for alkyl having 1 to 4 carbon atoms in the normal chain.

The terms "alkoxy" or "alkylthio" denote an alkyl group as described above bonded through an oxygen linkage (—O—) or a sulfur linkage (—S—), respectively. The term "alkyloxycarbonyl", as used herein, denotes an alkoxy group bonded through a carbonyl group. The term "alkylcarbonyloxy", as used herein, denotes an alkyl group bonded through a carbonyl group which is, in turn, bonded through an oxygen linkage. The terms "monoalkylamino" or "dialkylamino" denote an amino group substituted by one or two alkyl groups as described above, respectively.

The term "alkenyl", as used herein alone or as part of another group, denotes such optionally substituted groups as described above for alkyl, further containing at least one carbon to carbon double bond. Exemplary substituents include one or more alkyl groups as described above, and/or one or more groups described above as alkyl substituents.

The term "alkynyl", as used herein alone or as part of another group, denotes such optionally substituted groups as described above for alkyl, further containing at least one carbon to carbon triple bond. Exemplary substituents include one or more alkyl groups as described above, and/or one or more groups described above as alkyl substituents.

The term "cycloalkyl", as used herein alone or as part of another group, denotes optionally substituted, saturated cyclic hydrocarbon ring systems, preferably containing 1 to 3 rings and 3 to 7 carbons per ring. Exemplary unsubstituted such groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, and/or one or more groups described above as alkyl substituents.

The term "cycloalkenyl", as used herein alone or as part of another group, denotes such optionally substituted groups as described above for cycloalkyl, further containing at least one carbon to carbon double bond forming a partially unsaturated ring. Exemplary substituents include one or more alkyl groups as described above, and/or one or more groups described above as alkyl substituents.

The terms "ar" or "aryl", as used herein alone or as part of another group, denote optionally substituted, homocyclic aromatic groups, preferably containing 1 or 2 rings and 6 to 12 ring carbons. Exemplary unsubstituted such groups include phenyl, biphenyl, and naphthyl. Exemplary substituents include one or more, preferably three or fewer, nitro groups, alkyl groups as described above and/or groups described above as alkyl substituents.

The terms "heterocyclo" or "heterocyclic", as used herein alone or as part of another group, denote optionally substituted fully saturated or unsaturated, aromatic or non-aromatic cyclic groups having at least one heteroatom in at least one ring, preferably monocyclic or bicyclic groups having 5 or 6 atoms in each ring. The heterocyclo group may, for example, have 1 or 2 oxygen atoms, 1 or 2 sulfur atoms, and/or 1 to 4 nitrogen atoms in the ring. Each heterocyclo group may be bonded through any carbon or heteroatom of the ring system. Exemplary heterocyclo groups include the following: thienyl, furyl, pyrrolyl, pyridyl, imidazolyl, pyrrolidinyl, piperidinyl, azepinyl, indolyl, isoindolyl, quinolinyl, isoquinolinyl, benzothiazolyl, benzoxazolyl, benzimidazolyl, benzoxadiazolyl, and benzofurazanyl. Exemplary substituents include one or more alkyl groups as described above and/or one or more groups described above as alkyl substituents.

The terms "halogen" or "halo", as used herein alone or as part of another group, denote chlorine, bromine, fluorine, and iodine.

The term "taxane", as used herein, denotes compounds containing a taxane moiety as described following. The term "taxane moiety", as used herein, denotes moieties containing the core structure (with numbering of ring system positions used herein shown):

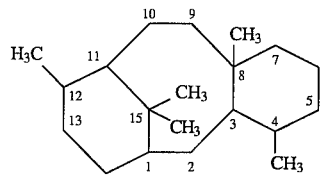

which core structure may be substituted and which may contain ethylenic unsaturation in the ring system thereof. Such moieties having an oxetane ring fused at the 4- and 5-positions, and an ethylenic double bond between C-11 and C-12, such as are found in paclitaxel, are preferred.

The term "hydroxy protecting group", as used herein, denotes any group capable of protecting a free hydroxyl group which, subsequent to the reaction for which it is employed, may be removed without disturbing the remainder of the molecule. Such groups, and the synthesis thereof, may be found in "Protective Groups in Organic Synthesis" by T. W. Greene, John Wiley and Sons, 1981, or Fieser & Fieser. Exemplary hydroxyl protecting groups include methoxymethyl, 1-ethoxyethyl, 1-methoxy-1-methylethyl, benzyloxymethyl, (β-trimethylsilylethoxy)methyl, tetrahydropyranyl, 2,2,2-trichloroethoxycarbonyl, t-butyl(diphenyl)silyl, trialkylsilyl, trichloromethoxycarbonyl, and 2,2,2-trichloroethoxymethyl.

The term "salt" includes acidic and/or basic salts formed with inorganic and/or organic acids and bases.

The term "chemical reduction method", as used herein, denotes a non-enzymatic reduction method; that is, the reducing agent employed is not a microorganism or enzyme, nor is a microorganism or enzyme employed for catalysis of the reduction.

The term "optically active agent", as used herein, refers to an optically active, especially optically pure, chiral organic compound, capable of forming a salt with a compound of the formula II. Thus, the resolution method of the present invention does not require use of an enzyme or microorganism.

The term "mixture", as said term is used herein in relation to stereoisomeric, such as enantiomeric compounds, includes mixtures having equal (i.e., a racemate in the case of an enantiomeric mixture) or non-equal amounts of stereoisomers.

Starting Materials

The starting materials employed in the present methods may be obtained according to the methods described in U.S. patent application Ser. No. 07/975,453, filed Nov. 12, 1992 by Patel et al. (Attorney Docket No. LD54), incorporated herein by reference, or by methods analogous thereto. Thus, the following Reaction Scheme may be employed for the preparation of compounds of the formula I.

Reaction Scheme

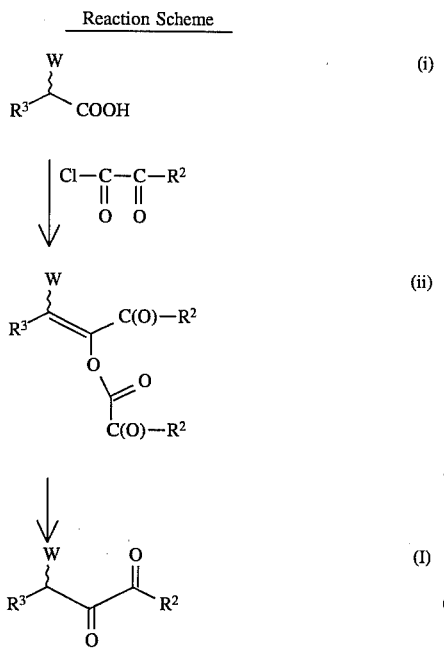

According to the above Reaction Scheme, compounds of the formula I may be prepared by reacting a compound (i) with an oxalyl chloride ester of the formula Cl—C(O)—C(O)—$R^2$, where $R^2$ is preferably unsubstituted lower alkoxy such as ethoxy or methoxy, for example, in anhydrous tetrahydrofuran (THF) in the presence of 4-dimethylaminopyridine (DMAP) and pyridine, to form a compound (ii). Compounds of the formula (i), and of the formula Cl—C(O)—C(O)—$R^2$, are commercially available or may readily be prepared by one of ordinary skill in the art. In the compound (i), W is preferably a group —NH—C(O)—$R^1$ where $R^1$ is —$R^5$ (such as where W is benzoylamino) or a urethane group where $R^1$ is —$OR^7$, most preferably where $R^7$ is unsubstituted alkyl (such as where W is t-butyloxycarbonylamino (BOC)), which may be prepared by reacting the corresponding compound (i) where W is amino (—$NH_2$) with the reagent $R^1$—C(O)—Cl or [$R^1$—C(O)]$_2$O. A racemate of a compound of the formula I may then be prepared from the compound (ii), for example, by heating the compound (ii) in ethanol in the presence of anhydrous $NaHCO_3$ or another mild base. Starting materials of the formula I which are other than racemic may be obtained, for example, by separation of the isomers of the racemate prepared above, or by addition of one or both of the enantiomers of the compound of the formula I in unequal portions to a racemic mixture thereof.

Preferred Compounds

It is preferred to prepare, according to the methods of the present invention, compounds of the formula II in which: W is —$NH_2$ or —NH—C(O)—$R^1$, where $R^1$ is aryl (especially phenyl) or alkoxy (especially t-butyloxy); $R^2$ is alkoxy, especially unsubstituted lower alkoxy (such as ethoxy or methoxy); and $R^3$ is aryl (especially phenyl), heterocyclo (especially furyl or thienyl) or alkyl. Compounds of the formula IIa or IIb are preferred.

Chemical Reduction Method

The reducing agent employed in the reduction method of the present invention may be any compound capable of reducing a compound of the formula I to form a compound of the formula II. Preferred reducing agents are hydrides, or hydrogen gas in the presence of a hydrogenation catalyst.

The chemical reduction method of the present invention is preferably conducted at a temperature of from about −78° C. to about 25° C.; and at a pressure of from about 1 atm to about 50 atm. The reduction may, for example, be completed over the course of about 15 minutes to about 16 hours, and is preferably conducted under an atmosphere of inert gas such as argon, or hydrogen where hydrogenation is employed. Solvents are preferably employed which are selected from organic or inorganic solvents such as alkanols (e.g., methanol, ethanol and the like), methylene chloride, tetrahydrofuran or ethylene dichloride ($ClCH_2CH_2Cl$). Amounts of solvents are preferably those where the formula I starting material is present in an amount of from about 1.0 to about 20% by weight, based on the combined weight of the solvent and formula I compound.

The starting compound of the formula I employed in the present reduction method may be present as a single stereoisomer having the R or S configuration with respect to the asymmetric carbon atom bearing the groups W and $R^3$ (that is, in a form substantially free of its opposite enantiomer), or as a mixture of the R and S stereoisomers, for example, as a racemate.

Preferred hydrides are metal hydrides or, especially, borohydrides of the formula $MBH_4$, where M is a metal (such as an alkali metal) or a tetraalkyl ammonium cation (such as $nBu_4N$, where nBu is n-butyl). Most preferred among hydrides is tetrabutyl ammonium borohydride. The molar ratio of hydride reducing agent to the starting compound of the formula I is preferably from about 5:1 to about 0.5:1.

Preferred hydrogenation catalysts include metals such as nickel, palladium and platinum, particularly where supported, such as on carbon, and most preferably employed with an acid such as aqueous HCl. The molar ratio of hydrogen gas to the starting compound of the formula I is preferably from about 1:1 to about 150:1; the molar ratio of hydrogenation catalyst to the starting compound of the formula I is preferably from about 1:20 to about 1:5.

Reduction of a compound of the formula I employing a hydride reducing agent can preferentially form anti enantiomers of the formulae IIb and IId relative to the formation of the corresponding syn enantiomers. Thus, in one preferred embodiment, the present invention provides a method for the chemical reduction of a compound of the formula I to stereoselectively form anti enantiomers of the formulae IIb and/or IId, comprising the steps of contacting said compound of the formula I with a hydride, preferably a borohydride, reducing agent capable of reducing said compound of the formula I to form said compounds of the formulae IIb and/or IId, and effecting said reduction.

Reduction of a compound of the formula I employing hydrogen gas in the presence of a hydrogenation catalyst as the reducing agent can preferentially form syn enantiomers of the formulae IIa and IIc relative to the formation of the corresponding anti enantiomers. Thus, in another preferred embodiment, the present invention provides a method for the chemical reduction of a compound of the formula I to stereoselectively form syn enantiomers of the formulae IIa and/or IIc, comprising the steps of contacting said compound of the formula I with hydrogen gas in the presence of a hydrogenation catalyst which is capable of reducing said compound of the formula I to form said compounds of the formulae IIa and/or IIc, and effecting said reduction.

"Stereoselective" formation of anti enantiomers of the formula II, as that term is used herein, denotes formation of the anti enantiomers in molar excess relative to the formation of the corresponding syn enantiomers, and preferably, formation of the anti enantiomers substantially free of the corresponding syn enantiomers. "Stereoselective" formation of syn enantiomers of the formula II, as that term is used herein, denotes formation of the syn enantiomers in molar excess relative to the formation of the corresponding anti enantiomers, and preferably, formation of the syn enantiomers substantially free of the corresponding anti enantiomers.

Separation

As discussed above, the products of the chemical reduction method of the present invention can include a mixture of stereoisomers. Any diastereomers present may be separated and purified, for example, by methods such as extraction, distillation, column chromatography, and, preferably, crystallization. It is preferred to separate any diastereomers present before separation of enantiomers. The enantiomers may be separated by the resolution method of the present invention.

In conducting the resolution method of the present invention, a compound of the formula II is contacted with an optically active agent. The optically active agent may be any optically active organic compound capable of forming diastereomeric salts upon contact with an enantiomeric mixture of the formula II compound. Preferred optically active agents are bases where the formula II compound is in acid form (in particular, where $R^2$ is —OH), most preferably amine compounds (i.e., compounds containing a primary, secondary or tertiary amine group), such as ephedrine, cinchonidine, naphthylethylamine and particularly α-methylbenzylamine (in particular, the (S)-(–)- or (R)-(+)- forms thereof), or any other basic compound which may be used as a basic resolving agent, used in optically active form.

The resolution method of the present invention is preferably conducted at a temperature of from about 0° C. to about 100° C.; and at a pressure of from about 1 atm to about 2 atm. The resolution may, for example, be completed over the course of about 10 minutes to about 24 hours, and is preferably conducted under an atmosphere of inert gas such as argon. The molar ratio of optically active agent to the compound of the formula II is preferably from about 1.2:1.0 to about 0.5:1.0. Solvents are preferably employed which are selected from organic or inorganic solvents such as ethyl acetate, acetonitrile, tetrahydrofuran and alcohols, with or without water. Amounts of solvents are preferably those where the formula II compound is present in an amount of from about 1 to about 20% by weight, based on the combined weight of the solvent and formula II compound.

The diastereomeric salts formed may be separated by any suitable technique, such as those described above for the separation of diastereomers, most preferably by crystallization, for example, where the diastereomeric salts are placed into a solvent in which one salt is relatively soluble and the other salt is relatively insoluble at a selected temperature. Upon obtaining a separated diastereomeric salt, the compound of the formula II may be regenerated by any suitable technique. For example, where the starting formula II compound of the present resolution method is an acid, as is preferred, that compound may be regenerated, following disastereomeric salt formation, by contact with an acid, most preferably a mineral acid (preferably in aqueous solution) such as HCl or potassium hydrogen sulfate ($KHSO_4$). Such regeneration of the acid form of the compound of the formula II is preferably conducted at a temperature of from about −5° C. to about 25° C.; at atmospheric pressure; and under an atmosphere of inert gas such as argon. The molar ratio of acid to the diastereomeric salt form of the compound of the formula II is preferably from about 3:1 to about 1:1. Solvents are preferably employed which are selected from organic or inorganic solvents such as ethyl acetate or methylene chloride, in amounts where the diastereomeric salt form of the compound of the formula II is about 1 to about 20% by weight, based on the combined weight of the solvent and salt compound.

As the compound of the formula II is preferably in acid form for contact with an optically active base in the present resolution method, it may be desirable to convert a compound of the formula II not already in acid form which is obtained, for example, by the present reduction method, to the acid form prior to resolution. Thus, for example, where the group —C(O)—$R^2$ is an ester group, the compound may be hydrolyzed to obtain a compound of the formula II bearing a carboxyl group. Hydrolysis may be conducted, for example, by contact with a base such as an alkali metal hydroxide (e.g., aqueous lithium hydroxide), although any suitable hydrolyzing agent may be employed. The hydrolysis is preferably conducted at a temperature of from about −5° C. to about 25° C.; at atmospheric pressure; and under an atmosphere of inert gas such as argon. The molar ratio of hydrolyzing agent to the compound of the formula II is preferably from about 2:1 to about 1:1. Solvents are preferably employed which are selected from organic or inorganic solvents such as tetrahydrofuran, dioxane, and alkanols such as methanol or ethanol, in amounts where the formula II compound is about 5 to about 20% by weight, based on the combined weight of the solvent and formula II compound.

It is preferred that the resolution method of the present invention achieve complete separation of the enantiomers. However, partial separation is also contemplated. For example, partial separation may be achieved in an initial resolution, and the resolution method conducted two or more times to achieve complete separation.

Utility

Taxanes are diterpene compounds containing a taxane moiety as described above. Of particular interest are taxanes containing a taxane moiety in which the 13-position contains a sidechain, which taxanes are exemplified by paclitaxel and analogs thereof. Pharmacologically active taxanes such as paclitaxel and analogs thereof may be used as antitumor agents to treat patients suffering from cancers such as breast, ovarian, colon or lung cancers, melanoma and leukemia.

The compounds obtained by the chemical reduction and resolution methods of the present invention are particularly useful as intermediates in the formation of the 13-position sidechain on a taxane moiety. Addition of the 13-position sidechain will yield a pharmaceutically useful taxane, including either a pharmacologically active taxane per se (such as paclitaxel or analogs thereof), or a sidechain-bearing taxane which may more readily be converted to a pharmacologically active taxane.

The compounds, especially the chiral compounds (that is, compounds which are substantially free of other isomers) obtained by the methods of the present invention may directly, or subsequent to optional modification (for example, protection of hydroxyl group(s), or reduction of the azide group (where W is —$N_3$) to form an amine group, the latter which may be substituted yielding the group —$NHR^5$ or —NH—C(O)—$R^1$), be used in the preparation of C-13 sidechain-bearing taxanes (especially C-13 acyloxy sidechain-bearing taxanes) such as those recited, and prepared by the methods described in, European Patent Publication No. 400,971, U.S. Pat. No. 4,876,399, U.S. Pat. No. 4,857,653, U.S. Pat. No. 4,814,470, U.S. Pat. No. 4,924,012, U.S. Pat. No. 4,924,011, and Kingston, *Pharm. Ther.*, Vol. 52, 1–34 (1991), especially U.S. patent application Ser. No. 08/171,792, filed Dec. 22, 1993 (Attorney Docket No. CT2262), all incorporated herein by reference.

Paclitaxel is preferably ultimately prepared as the C-13 sidechain-bearing taxane. Thus, for example, the compound (2S,3S)-N-benzoyl-3-phenylisoserine (i.e., 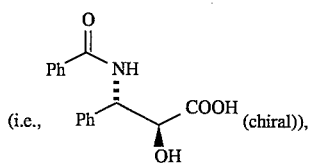 (chiral)), may be contacted with $CH_2N_2$ to form the corresponding methyl ester, and the methyl ester converted to the oxazoline compound

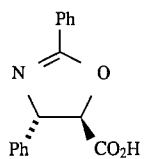

by contact, sequentially, with methylsulfonyl chloride and triethylamine, followed by hydrolysis with lithium hydroxide. Alternatively, the compound (2R,3S)-N-benzoyl-3-phenylisoserine (i.e., 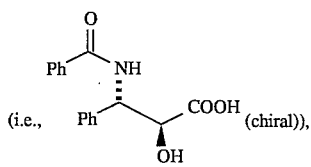 (chiral)), may be contacted with $CH_2N_2$ to form the corresponding methyl ester, and the methyl ester converted to the oxazoline compound

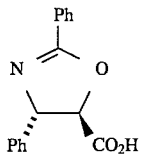

by contact, sequentially, with an acid such as pyridinium p-toluene sulfonic acid, followed by hydrolysis with lithium hydroxide. The oxazoline compound may then be coupled with a taxane moiety in accordance with the aforementioned U.S. patent application Ser. No. 08/171,792.

The present invention is further described by the following Examples which are illustrative only, and are in no way intended to limit the scope of the present claims.

EXAMPLE 1

Preparation of Racemic Starting Material
2-Keto-3-(N-benzoylamino)-3-phenyl propionic acid ethyl ester
(a) Benzoyl phenylglycine

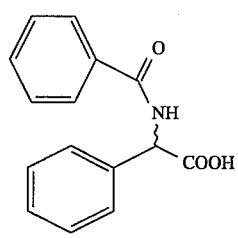

To (DL)-phenylglycine (9 g, 60 mole) in aqueous NaOH (1N, 180 ml) at 0° C. was added dropwise neat benzoyl chloride (PhCOCl) (7.73 ml, 66 mole) over a period of 5 minutes. The resulting solution was stirred for an additional 1 hour. The reaction solution was washed with ethyl acetate (EtOAc) (20 ml×2), then neutralized by 6N HCl and extracted with EtOAc (60 ml×2). The combined EtOAc layer was washed with brine (30 ml×2), dried over $MgSO_4$, filtered and concentrated to give a residue. The residue was crystallized from EtOAc/hexane to give 10.65 g of benzoyl phenylglycine as a white solid (70% yield, first crops). (The title product is also commercially available.)

(b) 3-Benzoylamino-3-phenyl-(ethyl, 2-oxalyl) propenoic acid, ethyl ester

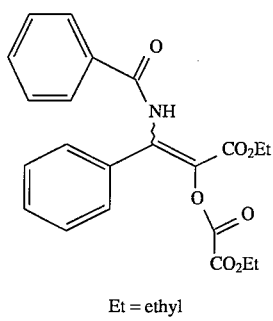

Et = ethyl

To a stirred solution of benzoyl phenylglycine prepared in step (a) (6.12 g, 24 mmole), 4-dimethylaminopyridine (100 mg, 0.82 mmole), and pyridine (5.86 ml, 72 mmole) in anhydrous tetrahydrofuran (THF) (24 ml) was added ethyl oxalyl chloride (5.35 ml, 48 mmole) at a rate to initiate gentle refluxing. (Refluxing at this point was not critical when sufficient refluxing (~3.5 h) as followed was employed). The mixture was then heated to maintain a gentle reflux for 3.5 hours. The reaction was monitored by thin layer chromatography (TLC) using 30% EtOAc in hexane as eluent ($R_f$ for the starting material was on the base line and $R_f$ for the products were 0.50 and 0.63 (E and Z isomers)). After cooling to room temperature, the mixture was treated with water (48 ml) and stirred vigorously at room temperature for ½ hour. The resulting organic layer was separated and the aqueous layer was extracted with EtOAc (36 ml×2). The combined organic layer was washed with brine (30 ml×1), dried over $Na_2SO_4$, filtered, concentrated, and crystallized from EtOAc/hexane to obtain 4.68 g of the enol ester title product (~63% yield, first crop—no attempt was made to get a second crop.)

(c) Racemic 2-Keto-3-(N-benzoylamino)-3-phenylpropionic acid ethyl ester

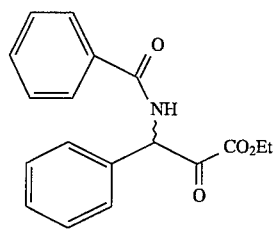

To a suspension of the enol ester title product prepared in step (b) above (6.0 g, 14.6 mmole) in 20 ml ethanol (EtOH) was added anhydrous $NaHCO_3$ (0.8 g, 9.49 mmole). The reaction mixture was refluxed for ½ hour. The reaction was monitored by TLC using 2% acetone in $CH_2Cl_2$ as eluent ($R_f$ for the starting materials were 0.50 and 0.75 (E & Z isomers) and $R_f$ for the product was 0.41). $NaHCO_3$ was filtered (if any) and the filtrate was concentrated to an oil. It was purified by column chromatography (($CO_2Et)_2$ was removed by column chromatography) (2% acetone/$CH_2Cl_2$) to give 5.6 g of the title product (~100% yield). (Crystallization was used for purification in subsequent preparation of the title product.) When the compound was stored in the freezer, it solidified.

m.p.: 80°–83° C.

TLC: $R_f$=0.43; Silica gel; 2% Acetone in $CH_2Cl_2$; UV and PMA Visualization.

EXAMPLE 2

Chemical Reduction Method Using Hydride
Preparation of (±)-N-Benzoyl-3-phenylisoserine, ethyl ester

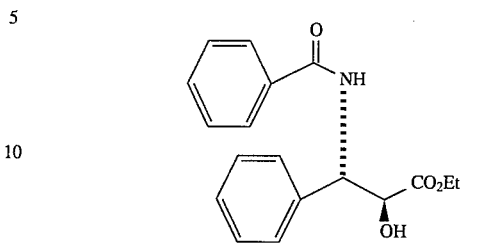

and

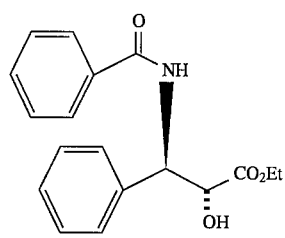

To a $CH_2Cl_2$ solution (30 ml) of the racemic title product of Example 1 (1 g) at −78° C. was added tetrabutyl ammonium borohydride (0.91 g) in one portion, and the resulting mixture allowed to stir at −78° C. for 15 minutes. The reaction mixture was diluted with ethyl acetate (EtOAc) (120 ml) and poured onto 1N HCl (80 ml) in a separatory funnel. The aqueous layer was separated and extracted with EtOAc (25 ml×2). The combined EtOAc layer was washed with brine (50 ml) and dried over $Na_2SO_4$. Filtration followed by removal of solvent in vacuo to dryness gave 1.01 g of crude alcohol as a white solid. The crude solid was dissolved in ~4 ml of hot methanol (MeOH); then set aside at room temperature for 10 minutes, 4° C. for 30 minutes. Filtration followed by washing with cold MeOH and drying gave 0.59 g of the pure title product alcohol, with an additional 80 mg as the second crop. The product was a racemic mixture of the (2S,3S) and (2R,3R) enantiomers of N-benzoyl-3-phenylisoserine, ethyl ester.

Total yield was 66.3% (0.67 g).

HNMR ($CDCl_3$) 67.82 (d, 2H, J=6.5 Hz), 7.56–7.10 (m, 8H), 5.61 (dd, 1H, J=6.8, 2.5 Hz), 4.63 (d, 1H, J=2.5 Hz), 4.17 (m, 2H), 1.12 (t, 3H, J=6.0 Hz). CNMR ($CDCl_3$) δ 171.65, 166.56, 136.54, 134.01, 131.58, 128.46, 128.40, 128.17, 127.54, 126.99, 72.80, 62.07, 55.40, 13.95.

EXAMPLE 3

Hydrolysis
Preparation of (±)-N-Benzoyl-3-phenylisoserine

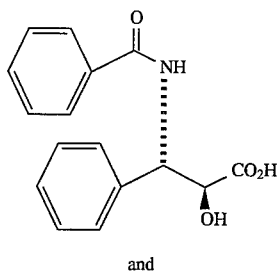

and

13

-continued

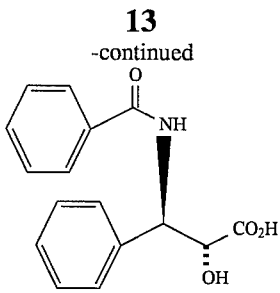

To a solution of the title product of Example 2 (3.0 g) in tetrahydrofuran (THF) (30 ml) at 0° C. was added 1N LiOH (19.1 ml) over a period of 10 minutes. The mixture was stirred at 0° C. for 60 minutes. It was then diluted with EtOAc (100 ml) and poured onto $H_2O$ (100 ml). The aqueous layer was extracted with EtOAc (100 ml) and the combined EtOAc layer was extracted with $H_2O$ (100 ml). The combined aqueous layer was cooled to 0° C. and acidified by 6N HCl to pH ~2. The resulting cloudy mixture was extracted with EtOAc (100 ml×2). The EtOAc layer was washed with brine (30 ml), dried over $Na_2SO_4$, filtered and concentrated to dryness to give 2.77 g of the title product acid as a foamy solid. The product was a racemic mixture of the (2S, 3S) and (2R,3R) enantiomers of N-benzoyl-3-phenylisoserine.

HNMR (CDCl$_3$)δ 8.75 (d, 1H, J=6.8 Hz), 7.83 (d, 2H, J=6.2 Hz), 7.58–7.42 (m, 4H), 7.36–7.21 (m, 3H), 5.28 (t, 1H, J=6.8 Hz), 4.34 (d, 1H, J=6.8 Hz ). CNMR (CDCl$_3$) δ 175.40, 167.42, 141.60, 136.18, 133.02, 130.02, 129.95, 129.55, 129.18, 128.80, 74.62, 57.20.

EXAMPLE 4

Resolution Method
Preparation of (2S,3S)-(–)-N-Benzoyl-3-phenylisoserine

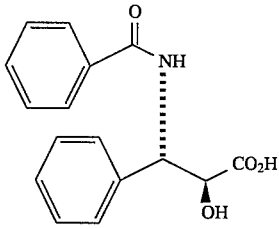

A. Formation of (S)-(–)-α-Methylbenzylamine Diastereomeric Salts, and Separation by Selective Crystallization To a stirred solution of the racemic acid title product of Example 3 (1.0 g) in $CH_3CN$ (45 ml) at 83° C. was added dropwise (S)-(–)-α-methylbenzylamine (0.47 ml) over a period of 5 minutes. A seed crystal was added, initiating selective crystallization of the salt of the title product. The resulting suspension was stirred for an additional 10 minutes at 83° C. It was filtered hot; washed with hot $CH_3CN$ (~3 ml), air-dried to give 0.35 g of the amine salt of the title product, $[α]_D$–55.5 (Cl, $CH_3OH$). (The product, methylated and then esterified with Mosher acid ((S)-(–)-α-methoxy-α-(trifluoromethyl)-α-phenyl-acetic acid), exhibited 98.5% optical purity).

HNMR (DMSO) δ 9.12 (d, 1H, J=6.0 Hz), 7.84 (d, 2H, J=6.5 Hz), 7.60–7.10 (m, 12H), 5.0 (t, 1H, J=5.4 Hz), 4.28 (q. 1H, J=6.1 Hz), 3.91 (d, 1H, J=5.4 Hz), 2.50 (s, 1H), 1.13 (d, 3H, J=6.1 Hz).

CNMR (DMSO) δ 176.45, 167.24, 142.80, 142.24, 136.50, 132.84, 130.31, 130.00, 129.76, 129.65, 129.19, 128.98, 128.38, 128.09, 76.00, 58.86, 51.64, 23.06.

14

B. Acidification of (S)-(–)-α-Methylbenzylamine Salt to Obtain Title Product

To a suspension of the (S)-(–)-α-methylbenzylamine salt of the title product (0.12 g) obtained in step A in ethyl acetate (5 ml) at 0° C. with vigorous stirring was slowly added 1N HCL (6.5 ml) over a period of 5 minutes. The resulting mixture was stirred for an additional 15 minutes. The aqueous layer was separated and extracted with EtOAc (5 ml×1). The combined organic layer was washed with half-saturated brine (6 ml), brine (6 ml), and dried over $Na_2SO_4$. Filtration followed by removal of solvent in vacuo gave 84 mg of the chiral acid title product as a white solid. $[α]_D$=–8.1 (Cl, $CH_3OH$); authentic $[α]_D$=–7.6 (Cl, $CH_3OH$). H&C NMR are consistent with those of the corresponding racemic acid (Example 3).

EXAMPLE 5

Chemical Reduction Method Using Hydrogen Gas and Pd/C Catalyst
Preparation of (±)-N-Benzoyl-3-phenylisoserine, ethyl ester

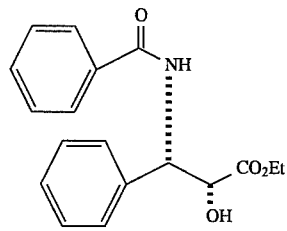

and

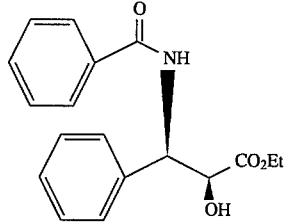

To a solution of the racemic title product of Example 1 (9.38 g, 30.13 mole) in ethanol (95%, 930 ml) was added, sequentially, 1N HCl (93.8 ml) and 5% Pd/C (0.94 g). This mixture was degassed three times with argon, and the argon then replaced with hydrogen with a balloon. The resulting mixture was stirred under the balloon hydrogen pressure (about 2 psi) for 16 hrs. The mixture was filtered through a pad of celite and the celite cake was washed with ethyl acetate (3×50 ml). The filtrate was diluted with ethyl acetate (1 L). The aqueous layer was separated and extracted with ethyl acetate (150 ml×1). The combined ethyl acetate layer was washed with brine (200 ml×1), dried over $Na_2SO_4$, filtered and concentrated. Chromatographic purification gave 8.62 g of a 5:1 mixture of syn:anti-alcohols. Crystallization of the mixture (8.62 g) from acetonitrile provided 4.9 g of pure racemic syn-alcohol ((2S,3R) and (2R,3S) enantiomers of N-benzoyl-3-phenylisoserine, ethyl ester) (~52% yield).

H NMR (DMSO) δ 8.75 (d, 1H, J=6.0 Hz), 7.82 (d, 2H, J=6.85 Hz), 7.65–7.15 (m, 7H), 5.80 (d, 1H, J=5.8 Hz), 5.21 (dd, 1H, J=5.8 & 3.6), 4.44 (dd, 1H, J=7.0 & 3.6), 4.00 (m, 2H), 1.02 (t, 3H, J=6.2 Hz)

EXAMPLE 6

Hydrolysis
Preparation of (±)-N-Benzoyl-3-phenylisoserine

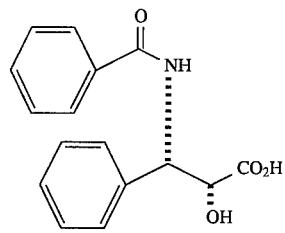

and

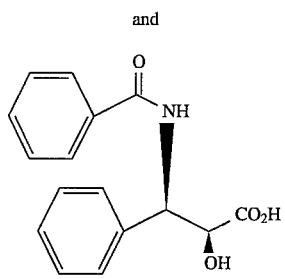

To a solution of the (±)syn-alcohol title product of Example 5 (2.91 g) in tetrahydrofuran (28 ml) at 0° C. was added dropwise aqueous LiOH (1N, 20.4 ml) over a period of 10 minutes. The resulting mixture was continued to stir at this temperature for 1 hour. The mixture was diluted with ethyl acetate (80 ml) and H$_2$O (80 ml). The aqueous layer was separated and extracted with ethyl acetate (60 ml). The combined ethyl acetate layer was washed with brine (60 ml). The combined aqueous layer was cooled at 0° C. and acidified to pH ~3 with 1N HCl (25 ml). The resulting mixture was extracted with ethyl acetate (200 ml×2) and the ethyl acetate layer was washed with brine (50 ml×2). The combined ethyl acetate (combined with previous ethyl acetate layer) was dried over Na$_2$SO$_4$, concentrated and dried to give 2.70 g of the syn-acid racemate title product ((2S,3R) and (2R,3S) enantiomers of N-benzoyl-3-phenylisoserine) as a white solid.

H NMR (DMSO) δ 8.56 (d, 1H, J=6.0 Hz), 7.84 (d, 2H, J=6.5 Hz), 7.60–7.10 (m, 7H), 5.44 (dd, 1H, J=7.0 & 2.8), 4.40 (d, 1H, J=2.8)

EXAMPLE 7

Resolution Method
Preparation of (2R,3S)-(−)-N-Benzoyl-3-phenylisoserine

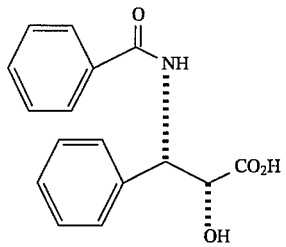

A. Formation of (R)-(+)-α-Methylbenzylamine Diastereomeric Salts, and Separation by Selective Crystallization To a suspension of the (±)syn-acid title product of Example 6 (0.2 g) in ethyl acetate (2.2 ml) was added R-(+)-α-methylbenzylamine (95 μl, 1.05 eq). The resulting homogeneous solution was allowed to stand at room temperature for 2 hours. It was then filtered and 0.268 g of the salt was obtained after drying. 100 mg of the dried salt was dissolved in hot ethanol (0.9 ml). The solution was set aside at room temperature for 16 hours. The resulting crystals were filtered and washed with cold ethanol, and dried in vacuo to afford 45 mg of the (R)-(+)-α-methylbenzylamine salt of the title product with optical rotation [α]$_D$–5.2 (c 1, CH$_3$OH).

B. Acidification of (R)-(+)-α-Methylbenzylamine Salt to Obtain Title Product

The (R)-(+)-α-methylbenzylamine salt of the title product obtained in step A was stirred in ethyl acetate (4 ml) and 5% aqueous KHSO$_4$ (4 ml). The aqueous layer was separated and extracted with ethyl acetate (4 ml×1). The combined organic layer was washed with brine (4 ml×1), dried over Na$_2$SO$_4$, filtered, and concentrated to dryness to provide 32 mg of the title (−)-syn-acid as a white solid with optical rotation [α]$_D^{25}$–11.7 (c 1, EtOH).

What is claimed is:

1. A method for the chemical reduction of a compound of the formula I:

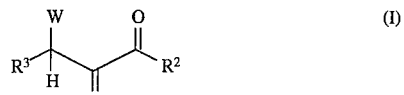

to form a compound of the formula II:

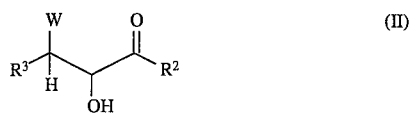

where

W is —N$_3$; —NH$_2$; or —NH—C(O)—R$^1$;

R$^1$ is aryl; or —O-alkyl;

R$^2$ is —OH: or —O-alkyl; and

R$^3$ is aryl; or heterocyclo;

comprising the steps of contacting said compound of the formula I with a reducing agent capable of reducing said compound of the formula I to form said compound of the formula II, and effecting said reduction.

2. The method of claim 1, wherein W is —NH$_2$ or —NH—C(O)—R$^1$, where R$^1$ is aryl or alkoxy; R$^2$ is alkoxy; R$^3$ is aryl or heterocyclo; and wherein the product of formula II is present in at least one of the following stereoisomeric forms IIa or IIb, alone or with other stereoisomers:

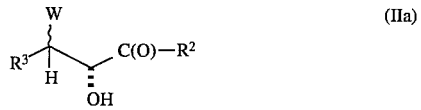

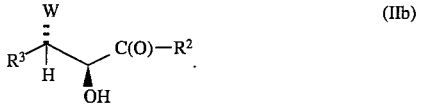

3. The method of claim 2, wherein the compound of the formula IIa or IIb is prepared as a racemate with its corresponding enantiomer.

4. The method of claim 1, wherein said reducing agent is a hydride.

5. The method of claim 4, wherein said reducing agent is a borohydride of the formula MBH$_4$, where M is a metal or a tetraalkyl ammonium cation.

6. The method of claim 5, wherein said reducing agent is tetrabutyl ammonium borohydride.

7. The method of claim 4, wherein anti enantiomers of the following stereoisomeric forms IIb and/or IId are stereoselectively formed:

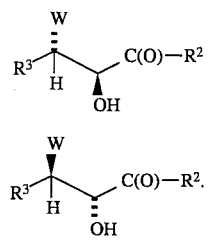

(IIb)

(IId)

8. The method of claim 7, wherein a racemate of compounds of the formulae IIb and IId is formed which is a racemic mixture of the (2S,3S) and (2R,3R) enantiomers of (±)-N-benzoyl-3-phenylisoserine, ethyl ester.

9. The method of claim 1, wherein said reducing agent is hydrogen gas in the presence of a hydrogenation catalyst.

10. The method of claim 9, wherein said hydrogenation catalyst is palladium or platinum supported on carbon.

11. The method of claim 9, wherein syn enantiomers of the following stereoisomeric forms IIa and/or IIc are stereoselectively formed:

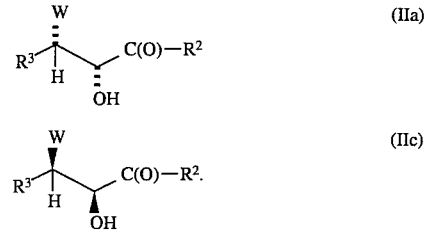

(IIa)

(IIc)

12. The method of claim 11, wherein a racemate of compounds of the formulae IIa and IIc is formed which is a racemic mixture of the (2R,3S) and (2S,3R) enantiomers of (+)-N-benzoyl-3phenylisoserine, ethyl ester.

13. The method of claim 2, wherein W is —$NH_2$ or —NH—C(O)—$R^1$ where $R^1$ is phenyl or t-butyloxy; $R^2$ is unsubstituted lower alkoxy; and $R^3$ is phenyl, furyl or thienyl.

* * * * *

UNITED STATES PATENT AND TRADEMARK OFFICE
CERTIFICATE OF CORRECTION

PATENT NO. : 5,602,272

DATED : February 11, 1997

INVENTOR(S) : Wen-Sen Li et al.

It is certified that error appears in the above-identified patent and that said Letters Patent is hereby corrected as shown below:

Column 16, line 50, structure (IIa)

" 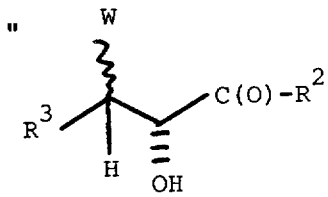 " should read -- 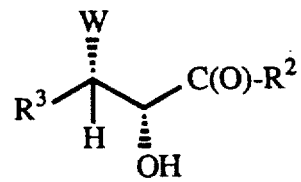 --.

(IIa)   (IIa)

Signed and Sealed this

Twenty-seventh Day of May, 1997

*Attest:*

BRUCE LEHMAN

*Attesting Officer*   *Commissioner of Patents and Trademarks*